US012558143B2

(12) United States Patent
Gander et al.

(10) Patent No.: US 12,558,143 B2
(45) Date of Patent: Feb. 24, 2026

(54) MEDICAL THERMOFUSION INSTRUMENT

(71) Applicant: Erbe Elektromedizin GmbH, Tuebingen (DE)

(72) Inventors: Jennifer Gander, Rottenburg (DE); Stefan Kaupp, Tuebingen (DE); Felix Bob, Rottenburg (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 291 days.

(21) Appl. No.: 18/512,202

(22) Filed: Nov. 17, 2023

(65) Prior Publication Data

US 2024/0164826 A1 May 23, 2024

(30) Foreign Application Priority Data

Nov. 21, 2022 (EP) .................................... 22208602

(51) Int. Cl.

*A61B 18/02* (2006.01)
*A61B 18/08* (2006.01)
*A61B 18/00* (2006.01)

(52) U.S. Cl.

CPC .. *A61B 18/085* (2013.01); *A61B 2018/00077* (2013.01); *A61B 2018/00083* (2013.01);
(Continued)

(58) Field of Classification Search

CPC ............. A61B 18/085; A61B 18/1442; A61B 2018/00077; A61B 2018/00083; A61B 2018/00428; A61B 2018/00601; A61B 2018/0063; A61B 2018/00964; A61B 2018/146

See application file for complete search history.

(56) References Cited

U.S. PATENT DOCUMENTS 5,527,313 A * 6/1996 Scott .................. A61B 18/1442 606/41
5,976,132 A * 11/1999 Morris .............. A61B 18/1445 606/49
(Continued)

FOREIGN PATENT DOCUMENTS

DE 10323533 B4 9/2021
EP 0853922 B1 2/2005
(Continued)

OTHER PUBLICATIONS

Extended European Search Report for European Patent Application No. 22208602.7-1126, dated Apr. 24, 2023; 14 pages.

*Primary Examiner* — Daniel W Fowler
(74) *Attorney, Agent, or Firm* — Fitch, Even, Tabin & Flannery LLP

(57) ABSTRACT

A current supply arrangement (22) is used for electrical supply of two electrodes (18, 19), as well as for mechanical force transmission in a thermofusion instrument. Due to the configuration of the two electrical conductors (23, 28) as upright arranged flat parts and the force concerned coupling thereof in an interlocking section (32), the electrical conductors (23, 28) can be used as mechanical stiffening elements, whereby a filigree, gap-free, easily and reliably sterilizable configuration is achieved. The current supply of the instrument (10) is provided via one single cable (20) only, which is provided only on one of the two jaws (11, 12).

15 Claims, 3 Drawing Sheets

(52) U.S. Cl.
CPC ................. *A61B 2018/0063* (2013.01); *A61B 2018/00964* (2013.01); *A61B 2560/0468* (2013.01)

(56) References Cited

U.S. PATENT DOCUMENTS

| | | | | |
|---|---|---|---|---|
| 2014/0214019 | A1 | 7/2014 | Baxter, III et al. | |
| 2020/0375654 | A1 | 12/2020 | Bob | |
| 2021/0052334 | A1 * | 2/2021 | Johnson ................. | A61B 34/35 |

FOREIGN PATENT DOCUMENTS

| | | | |
|---|---|---|---|
| EP | 1595509 | A2 | 11/2005 |
| EP | 1153578 | B1 | 3/2007 |
| EP | 3744278 | A1 | 12/2020 |
| WO | 2009149799 | A1 | 12/2009 |

* cited by examiner

MEDICAL THERMOFUSION INSTRUMENT

CROSS REFERENCE TO RELATED APPLICATION

This application claims the benefit of European Patent Application No. 22208602.7, filed Nov. 21, 2022, which is incorporated herein by reference in its entirety.

TECHNICAL FIELD

The invention refers to a medical thermofusion instrument as can be used, for example, for sealing and if applicable also separating of biological tissue, particularly blood vessels and similar hollow organs.

BACKGROUND

Thermofusion instruments are used during surgical operations on a patient and have to be either disposed of or else cleaned and sterilized subsequently. The latter imposes high demands concerning mechanical, thermal and chemical resilience of the instrument and concerning its as most as possible gap-free configuration, in order to allow a reliable cleanability. In spite of repeated cleaning cycles, its function has to be maintained.

Thermofusion elements are generally known. For example, EP 1 595 509 A2 discloses such a forceps-like instrument, the two jaws of which are movably supported on one another at a hinge. One of the jaws serves for current supply for both sealing electrodes cooperating during thermofusion. While the electrical current for one of the electrodes can be directly supplied in the respective jaw, the current for the other electrode is conducted via the hinge. For this purpose, in the hinge area an insulating body having a ring groove is provided in which a ring sliding contact for the other jaw is located.

A thermofusion instrument with current supply via one of the involved jaws is also known from EP 3 744278 A1. The jaws are manufactured from plastic-coated metal there, so that during compressing of biological tissue the required mechanical forces can be transmitted from the grip ends reliably onto the forceps-like tool.

Another variant of such instruments is known from WO 2009/149799 A1. The hinge transmitting current from one of the jaws to the other is configured as switch so that the electrically conductive connection is only enabled when closing the instrument.

In addition, DE 103 23 533 B4 discloses a thermofusion instrument with current supply to the electrodes via one of the two jaws. Thereby the metal body of the jaw is used as conductor for one pole, while a wire provided on the other jaw is used as second pole.

Finally, a forceps-like thermofusion instrument is known from EP 1 153 578 B1 in which a hinge bolt is provided in order to transmit current from a conductor made of sheet metal through the hinge to the other jaw.

SUMMARY

For the configuration of a medical thermofusion instrument beside the sterilization ability and the re-sterilization ability, also a high precision and a high mechanical resilience is of importance. Particularly, such instruments shall also be designed as filigree as possible without sacrifices concerning stability as well as tightness and the protection of potential electronic components, which can be arranged in the instrument.

Therefore, it is one object of the invention to provide a concept for a medical thermofusion instrument that can be reliably sterilized due to its basic structure and its practical configuration and is thereby filigree and convenient to handle.

This object is solved by means of the thermofusion instrument as described herein.

The thermofusion instrument according to the invention comprises two jaws that are pivotably supported on one another at a hinge. Only one of the two jaws is provided with a cable and comprises a current supply arrangement via which the two electrodes can be supplied with current and voltage. The current supply arrangement comprises two conductors formed by flat band-shaped elements. These elements can be completely or partly configured as metal sheet elements or investment cast elements. Thereby one of the elements is flat and the other of the elements is largely flat as well, but configured in a cranked manner at one location. In doing so, the two conductors formed by flat elements can be arranged in a first section in the proximity of the hinge in a manner lying in a common plane, whereby they join one another at a joint filled with rigid electrically insulating material. In another, second section extending from the hinge further away toward a grip end of the jaw, the two conductors can be arranged with distance adjacent to one another with their flat sides facing toward each other. Thereby they can be preferably arranged upright in the jaw, i.e. within planes relative to which the hinge axis extends orthogonal. This allows the use of both flat elements, not only for current transmission, but also for creation of the desired bending resistance of the respective jaw that consists apart therefrom of plastic.

The joint, at which the two sections of the elements are arranged in a manner adjacent to one another, thereby serves the transmission of forces between the elements within the jaw. The latter is thereby stiffened and achieves a high bending resilience. In doing so, biological tissue can be firmly held and hollow organs can be reliably compressed without overloading the thermofusion instrument also during repeated use and after multiple sterilizations. Thus, always good fusion results can be achieved.

The first conductor and the first electrode electrically connected therewith can be seamlessly monolithically configured. Due to avoiding contact locations, reliability is inherently provided.

The hinge is preferably electrically conductively configured in order to connect the second conductor electrically with the second electrode. For this purpose, the hinge preferably comprises two hinge halves that are in electrical and friction-fit contact at contact surfaces assigned to one another. It is possible to assign one or more spring elements to the contact surfaces in order to guarantee a continuous electrical contact therebetween. Preferably at least one of the contact surfaces of the two hinge halves is configured in a truncated cone-shaped manner, which allows a good contact establishment. Preferably the contact surfaces of the two hinge halves are configured matching one another in a truncated cone-shaped manner.

In a preferred embodiment the joint between the two elements is configured in a special manner, particularly advantageous with regard to force transmission. For this purpose, the joint can comprise an interlock section in which one of the elements comprises a recess and the other of the two elements comprises a projection fitting into the recess.

The recess and the projection, however, do not abut against each other, but define a respective joint. The joint is preferably (2-shaped, which allows on one hand a good electrical insulation and on the other hand a good force transmission between the elements.

It is advantageous, if the projection is configured in a disc-shaped manner and comprises a neck section by means of which it is seamlessly monolithically connected with the remaining element. The neck section is thereby preferably narrower than the disc-shaped (head) section, whereby a form-fit interlocking between the two flat elements can be achieved. The disc-shaped head can have a circular arc shape or also otherwise shaped edge.

In the second section of the jaw extending from the hinge toward the handle the two elements are preferably inserted into an insulating body. This insulating body secures a position of the elements relative to one another prior to overmolding with additional plastic that finally fills the joint in the interlocking section and fixates the elements in correct position relative to one another. The accurate positioning of the elements relative to one another can be particularly guaranteed also from the hinge halves, which, forming respective metal elements, are welded to the involved elements prior to overmolding with plastic and which can be exactly positioned within an injection mold.

BRIEF DESCRIPTION OF THE DRAWINGS

Embodiments of the invention are derived from the drawing as well as the respective description. The drawing shows.

DETAILED DESCRIPTION OF THE DRAWINGS

Figure 1:
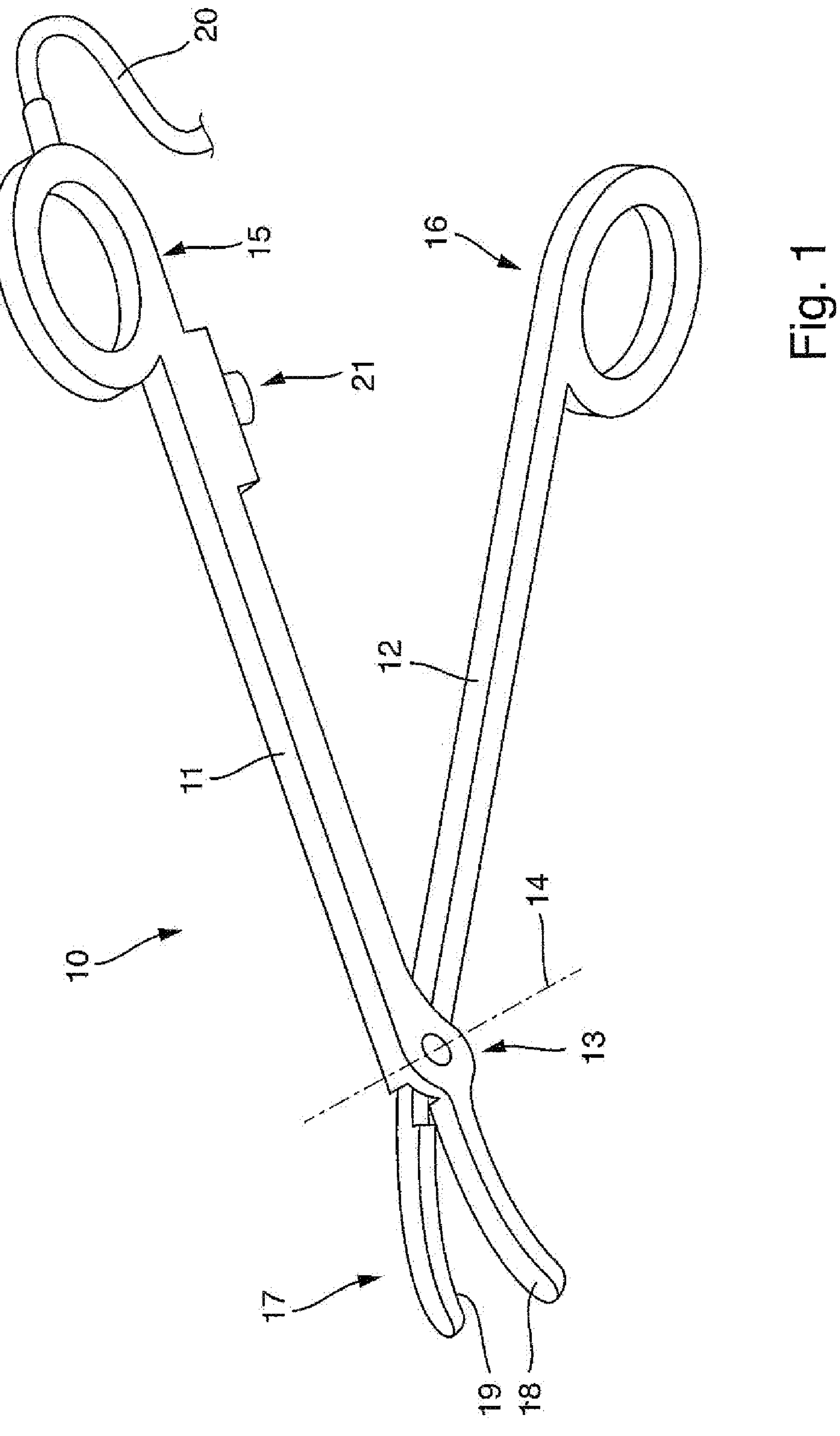
FIG. 1 an embodiment of a thermofusion instrument in a perspective overview illustration, FIG. 2 electrodes and the associated current supply arrangement, particularly in the hinge area, in perspective explosion illustration, FIG. 3 a joint section between conductor elements of the current supply arrangement according to FIG. 2 in an illustration in part, FIG. 4 hinge halves of the hinge of the thermofusion instrument in a side view, FIG. 5 the current supply arrangement of the thermofusion instrument according to the invention in top view, FIG. 6 conductor elements of the current supply arrangement in top view and explosion illustration, FIG. 7 a cross-sectional illustration of the handle area of the jaw with current supply arrangement.

FIG. 1 illustrates a thermofusion instrument 10 that can be cleaned and repeatedly sterilized, which is configured as tissue forceps for fusion of biological tissue. It comprises a first jaw 11 and a second jaw 12 that are pivotably supported on one another around a hinge axis 14 at a hinge 13. The two jaws 11, 12 comprise handle ends 15, 16 proximal relative to the hinge 13 and a forceps-like tool 17 distal relative to the hinge 13. The tool 17 comprises a first electrode 18 being part of the first jaw 11 and a second electrode 19 being part of the second jaw 12 on surfaces facing one another. The electrodes 18, 19 serve to supply current to tissue held and compressed in the tool 17 in order to heat it and to thereby cause tissue fusion.

For current supply of the two electrodes 18, 19 a multi-core current supply cable 20 is provided that is only connected to first jaw 11. On the contrary, second jaw 12 does not have a cable connection.

Switching means can be arranged on first jaw 11, such as a switch 21 that enables a current flow to the electrodes 18, 19 during closing of the jaws 11, 12, i.e. connects them with a generator to which the thermofusion instrument 10 is connected via current supply cable 20. In or at switch 21 an electronic circuit can be provided to control or influence the operation of the thermofusion instrument 10 in a suitable manner. For example, the electronic circuit can decrease or interrupt current supply to the electrodes 18, 19 in specific situations, e.g. if a sufficient fusion result is achieved.

Figures 2, 3:
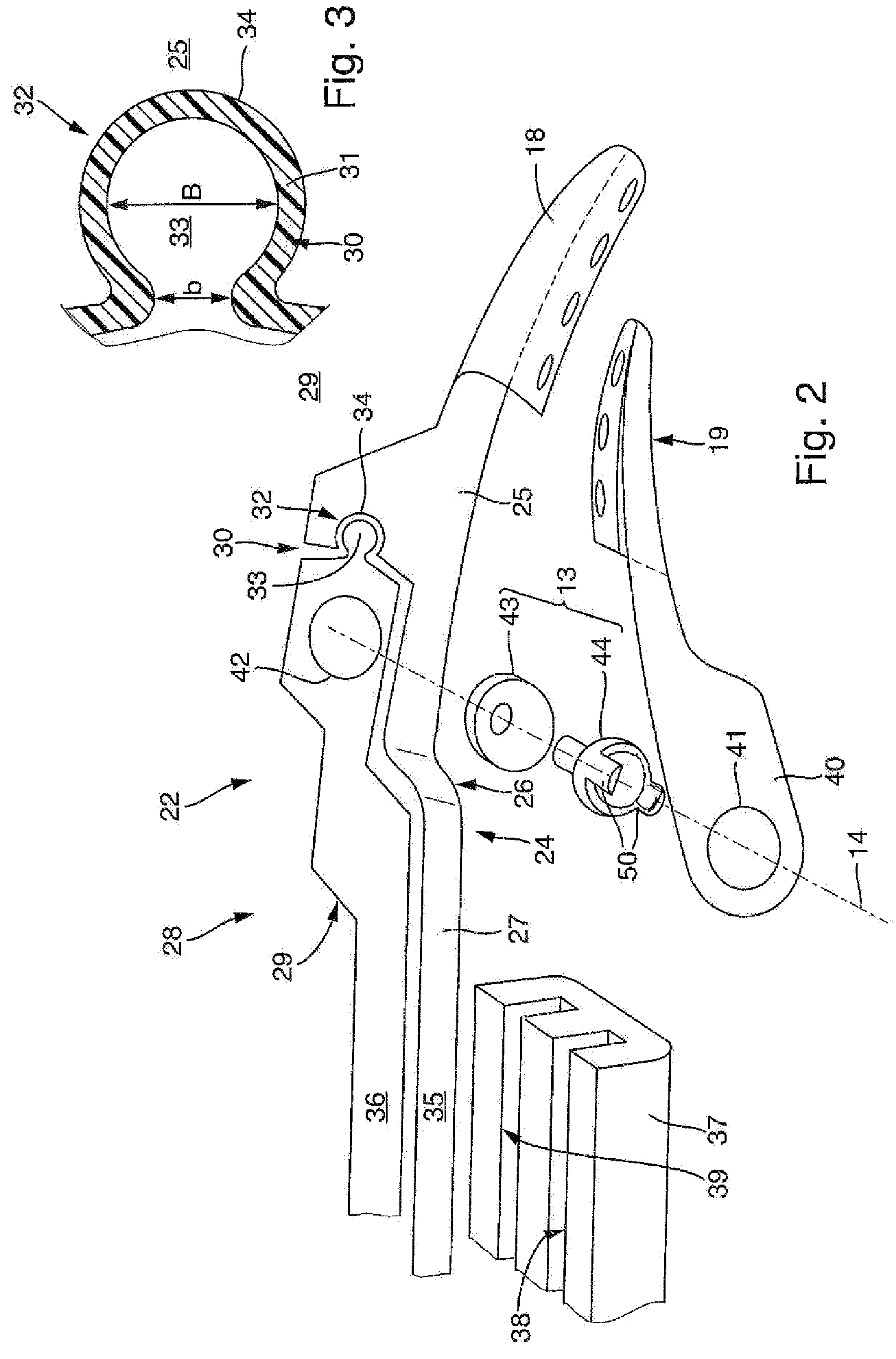

The jaws 11, 12 of thermofusion instrument 10 consist predominantly of plastic, whereby a current supply arrangement 22 is arranged in the first jaw 11, which is individually apparent from FIG. 2, at least in sections. The jaw 12 can contain a stiffening element of metal. On the contrary, the current supply arrangement 22 serves as stiffening element in the jaw 11.

A first conductor 23, which is preferably configured by a strip-shaped flat element 24, e.g. a metal sheet element, is part of the current supply arrangement 22. This element 24 can consist of sheet metal, but alternatively also entirely or partly of cast material. This element 24 comprises first electrode 18 to which a flat section 25 adjoins proximally. This section 25 is located in a plane E1 (see FIG. 5) to which the hinge axis 14 extends orthogonally. This section 25 extends around the hinge 13 and projects slightly beyond the hinge axis 14 in proximal direction. Then it transitions at a crank 26 into a second section 27 of conductor 23 that in turn is located in a second plane E2, which is parallel to first plane E1 mentioned above and to which the hinge axis 14 is orientated substantially orthogonal as well.

In addition, a second conductor 28 configured as flat even element 29 is part of the current supply arrangement 22. The element 29 can consist of sheet metal, but alternatively also entirely or partly of cast material. This element 29 is located in a common plane together with section 25 of conductor 23, i.e. in the plane E1, at least in the area of hinge 13. Together with section 25 of conductor 23 the element 29 here defines a joint 30 that is individually illustrated in FIG. 3 in an enlarged manner. The joint 30 is filled with plastic 31 that is molded during production of the first jaw 11 around the current supply arrangement 22 and thereby enters and fills joint 30.

The joint 30 has at least such a width that the dielectric strength of plastic 31 inside joint 30 (and also at other locations) is not exceeded with the used coagulation voltages. The dielectric strength is preferably in a range of multiple hundred volts and exceeds 500 V, for example, in order to guarantee the required operation reliability. Preferably the width of the joint, i.e. the distance between the elements 24, 29 in the joint 30 (and also at other locations), is at least as large as the thickness of the elements 24, 29 to be measured orthogonal to their flat sides, e.g. the thickness of the used sheet metal.

Preferably the joint 30 comprises one or more interlockings 32, as apparent from FIG. 2, and as is individually illustrated in FIG. 3. The interlocking 32 is formed by a projection 33 of the one element, e.g. element 29, which engages in a recess 34 of the other element, e.g. element 24. For example, the joint 30 can be configured in this area in an Ω-shaped, dovetail-shaped rounded dovetail-shaped or similar manner. Preferably the projection 33 comprises a maximum width B (FIG. 3) that is longer than the width b of this projection in a web or connection area in which the preferably disc-shaped projection 33 transitions into the remaining element 29. Preferably the projection 33 is a monolithic part of element 29.

While the projection 33 is assigned to element 29 and the recess 34 is assigned to element 24 in FIGS. 2 and 3, the assignment can also be made vice versa. It is in addition possible to provide multiple of such projection/recess pairs having identical or alternating orientation.

While the respective sections of the elements 24, 29 are arranged to be located in a common plane E1 in the area of hinge 13, they are arranged in a second section proximal relative to the hinge axis 14 with distance A parallel to one another (see FIG. 5) so that they face one another with two of their flat sides and they face away from each other with the respective other flat sides. The respective sections 35, 36 of the two conductors 23, 28 can be embedded in a respective insulating body 37, e.g. of plastic, for insulation and spacing. For this purpose, it can comprise respective holding slits 38, 39 extending longitudinally through insulating body 37.

The second conductor 28 is connected via hinge 13 with second electrode 19, which can be configured as sheet metal bending part, as cast part (e.g. investment cast part or the like) and comprises a flat section 40 extending toward hinge 13. The section 40 comprises an opening 41 that is orientated concentrically relative to hinge axis 14. Similarly element 29 comprises an opening 42, which is concentric relative to hinge axis 14.

A first hinge half 43 and a second hinge half 44, which are preferably made of electrically conductive material, particularly metal, in order to establish an electrical connection between second conductor 28 and element 40, are part of hinge 13. The hinge halves 43, 44 form an electrically conductive pivot joint defining the hinge axis 14.

Figure 4:
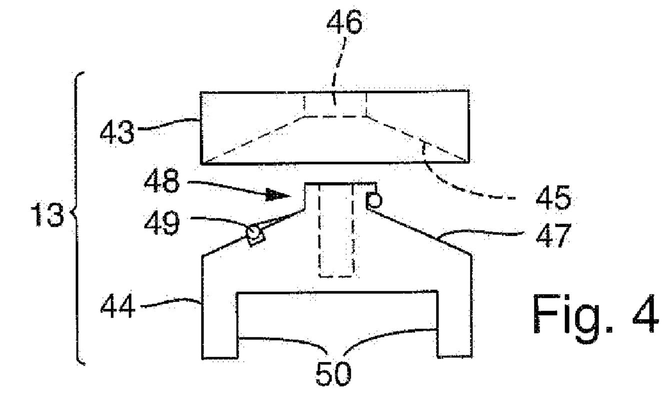

The configuration of hinge 13 is apparent from FIG. 2 and more particularly from FIG. 4:

The hinge half 43 is formed by a flat cylindrical body in which a seat opening 49 can be formed. The seat opening has preferably a truncated cone shape transitioning into a cylinder section 46. If element 29 is a metal sheet part, first hinge half 43 is welded or otherwise electrically conductively and mechanically rigidly connected to one of the elements 29 or 40, in the example here with the edge of opening 42 of the metal sheet part. If element 29 is configured as cast part at least in the area of the hinge, the hinge half 43 can be monolithically configured therewith forming part of the cast part.

The second hinge half 44 comprises a contact surface 47 being complementary to the contact surface 45, whereby contact surface 47 can transition into a cylindrical extension 48. The latter can be provided with a securing bore serving to receive a non-illustrated securing element in order to secure hinge 13 in assembled condition.

As an option, in or on the contact surface 45 and/or contact surface 47 one or more spring means 49 can be arranged, e.g. a spring ring, which can be arranged in a groove, which is here, for example, a groove formed respectively in the contact surface 47 and/or the extension 48.

Figure 5:
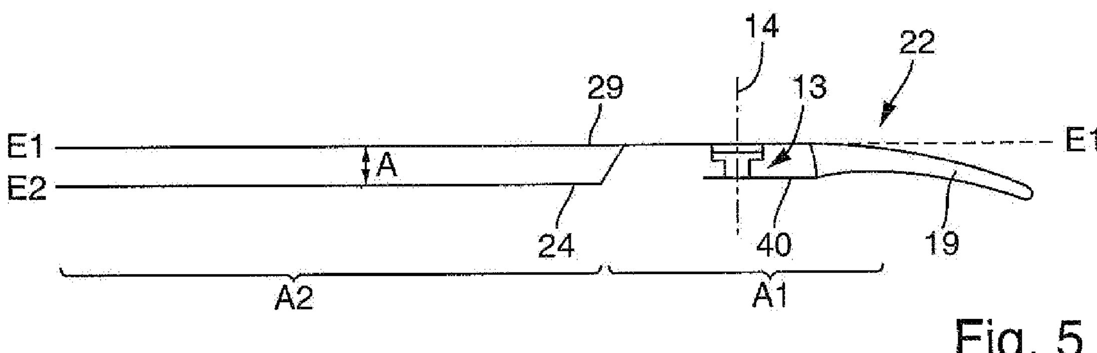

FIG. 5 illustrates first element 24, second element 29, hinge 13 and element 40 in top view. As apparent, the elements 24, 29 are located inside the common plane E1 in the area of hinge 13, while in the second section distanced proximal from hinge 13 they are arranged in planes E1, E2, which are parallel to one another.

Figure 6:
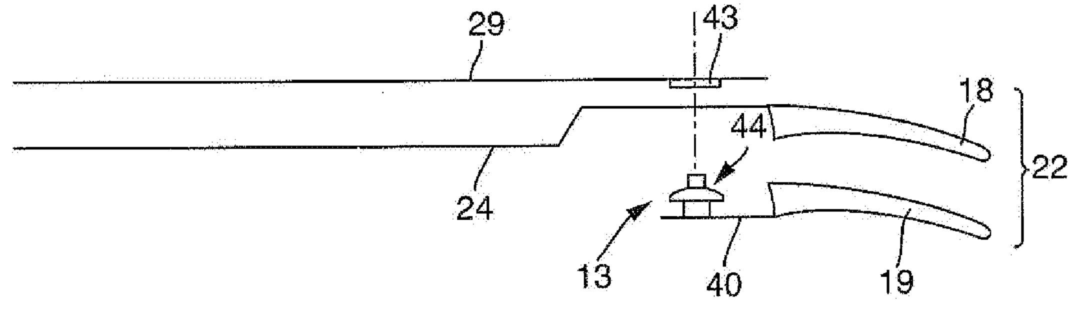

For improved clarification of the configuration of hinge 13 and the elements 29, 24, 40 reference is made in addition to FIG. 6. As apparent, first hinge half 43 is connected with first element 29, while second hinge half 44 is connected with element 40, e.g. by means of two extensions 50. Between the two extensions 50 a distance is provided, which can be used by other elements. For example, a knife channel can be provided in the thermofusion instrument 10 extending through hinge 13. For example, such a knife can be arranged to be forwarded in distal direction, i.e. can be translationally movably arranged in the tool 17, in order to cut fusioned tissue in the tool 17.

If element 40 is a metal sheet part, the hinge half 43 can be welded to the element 40, e.g. in that the extensions 50 are welded to the edge of opening 41. Alternatively, the element 40 and the hinge half 44 can be provided as cast part, e.g. investment cast part. They can be produced by one single cast part or by cast parts that are subsequently connected to one another.

Figure 7:
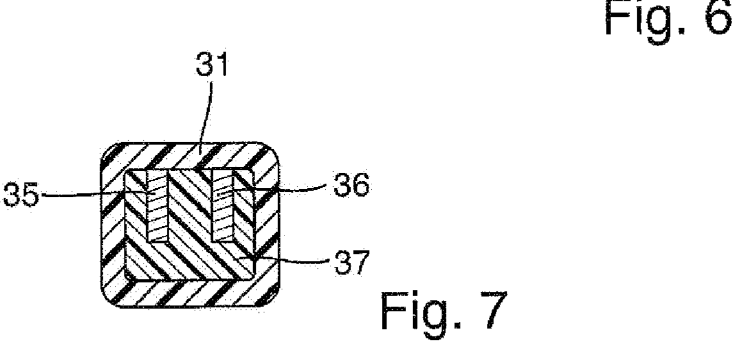

For manufacturing the fusion instrument 10, first the elements 24, 29, 40 can be provided. If they are not already provided, in a second step hinge halves 43, 44 are created on the elements 29, 40 or are connected therewith. The elements 24, 29 are then inserted in the insulating body 37. Alternatively, the insulating body is produced on the elements 24, 29 or around the latter, for example by means of primary shaping. The unit consisting of hinge 13, current supply arrangement 22 and insulating body 37 created thus far is then inserted into an injection mold and coated entirely with plastic 31 that then also fills the joint 30, as mentioned above. The cross-section through jaw 11 results, as illustrated in FIG. 7.

The resulting jaw 11 is configured in a gap-free manner and can be configured in a filigree manner and thereby mechanically stable, in spite of using plastic as basic material. The current supply arrangement 22 fulfills a double function, namely the current supply to the electrodes 18, 19 and the mechanical reinforcement of jaw 11. The actuating force originating from handle ends 15, 16 is transmitted by the two elements 24, 29 in direction toward tool 17. The fraction of the force transmitted via element 29 is transmitted via interlocking section 32 from element 29 onto section 25 of element 24 and thus finally onto electrode 18.

In the thermofusion element according to the invention, a current supply arrangement 22 is used for electrical supply of the two electrodes 18, 19 as well as for mechanical force transmission. Due to the configuration of the two electrical conductors 23, 28 as upright arranged flat parts and the force concerned coupling thereof in an interlocking 32, the electrical conductors 23, 28 can be used as mechanical stiffening elements, whereby a filigree, gap-free, easily and reliably sterilizable configuration is achieved. The current supply if instrument 10 is provided via one single cable 20 only, which is provided only on one of the two jaws 11, 12.

LIST OF REFERENCE SIGNS

- 10 thermofusion instrument
- 11 first jaw
- 12 second jaw
- 13 hinge
- 14 hinge axis
- 15, 16 handle ends
- 17 tool
- 18 first electrode
- 19 second electrode
- 20 current supply cable
- 21 switch
- 22 current supply arrangement
- 23 first conductor
- 24 first element
- 25 section of conductor 23 and element 24
- 26 crank of element 24

27 second section of conductor 23 and element 24
28 second conductor
29 second element
30 joint
31 plastic
32 interlocking section
33 projection
34 recess
35 second section of first conductor 23/element 24
36 second section of second conductor 28/element 29
37 insulating body
38 holding slit for section 35 of first conductor 23
39 holding slit for section 36 of second conductor 28
40 element with electrode 19
41 opening in section 40
42 opening in element 29
43 first hinge half
44 second hinge half
45 seat opening and contact surface
46 cylinder section
47 contact surface
48 extension
49 spring means
50 extensions of second hinge half 44

The invention claimed is:

1. A medical thermofusion instrument (10) comprising:

a first jaw (11) and a second jaw (12) that are pivotably supported with respect to one another at a hinge (13) that defines a hinge axis (14);

a current supply arrangement (22) arranged in the first jaw (11) and comprising a first conductor (23) and a second conductor (28), wherein the first conductor (23) is electrically connected with a first electrode (18) provided on the first jaw (11) and the second conductor (28) is electrically connected with a second electrode (19) provided on the second jaw (12);

wherein the first and second conductors (23, 28) are formed by flat strip-shaped elements (24, 29); and the current supply arrangement (22) comprises a first section (A1) in which portions (25) of the first and second conductors (23, 28) are arranged in a common plane (E1) and adjacent to one another at a joint (30) filled with a rigid electrically insulating material (31).

2. The medical thermofusion instrument according to claim 1, wherein the first and second conductors (23, 28) each have a flat side and the current supply arrangement (22) comprises a second section (A2) in which the first and second conductors (23, 28) are adjacent to one another such that the flat side of the first conductor (23) is spaced apart from the flat side of the second conductor (28).

3. The medical thermofusion instrument according to claim 2, wherein in the second section (A2), the second conductor (23) extends along a first plane (E1) and the first conductor (28) extends along a second plane (E2) that is spaced apart from the first plane (E1), wherein the first and second planes (E1, E2) are orthogonal to the hinge axis (14).

4. The medical thermofusion instrument according to claim 1, wherein the first conductor (23) and the first electrode (18) are configured in a seamless monolithic manner.

5. The medical thermofusion instrument according to claim 1, wherein the hinge (13) is electrically conductive and that the second conductor (28) is electrically connected with the hinge (13).

6. The medical thermofusion instrument according to claim 1, wherein the second electrode (19) is electrically connected with the hinge (13).

7. The medical thermofusion instrument according to claim 1, wherein the hinge (13) comprises two hinge portions (43, 44) that are in electrical and friction-fit contact with one another at respective contact surfaces (45, 47) thereof.

8. The medical thermofusion instrument according to claim 7, wherein one of the contact surfaces (45, 47) has a concave truncated cone shape.

9. The medical thermofusion instrument according to claim 7, wherein one of the contact surfaces (45, 47) has a convex truncated cone shape.

10. The medical thermofusion instrument according to claim 7, wherein a spring element (49) is arranged between the contact surfaces (45, 47).

11. The medical thermofusion instrument according to claim 1, wherein the joint (30) comprises an interlocking section (32) in which one of the flat strip-shaped elements (24, 29) comprises a recess (34) and an other of the flat strip-shaped elements comprises a projection (33) positioned in the recess (34).

12. The medical thermofusion instrument according to claim 11, wherein the projection (33) has an arcuate configuration and is connected to a remainder of the other of the flat strip-shaped elements via a neck section in a seamless monolithic manner.

13. The medical thermofusion instrument according to claim 12, wherein the neck section has a width (b) which is smaller than a maximum width (B) of the projection (33) measured in a same direction.

14. The medical thermofusion instrument according claim 2, wherein the flat strip-shaped elements (24, 29) are disposed in an insulating body (37) in the second section (A2).

15. The medical thermofusion instrument according to claim 1, wherein the flat strip-shaped elements (24, 29) are overmolded by a plastic mass (31).

* * * * *